United States Patent
Kuybeda et al.

(10) Patent No.: US 11,706,380 B2
(45) Date of Patent: Jul. 18, 2023

(54) RADIOMETRIC CAMERA WITH BLACK BODY ELEMENTS FOR SCREENING INFECTIOUS DISEASE CARRIERS AND METHOD FOR CALIBRATING A THERMAL CAMERA HAVING INTERNAL BLACK BODY ELEMENTS

(71) Applicant: Adasky, Ltd., Yokneam Illit (IL)

(72) Inventors: Oleg Kuybeda, Portland, OR (US); Igor Ivanov, Haifa (IL); Yair Alpern, Kiryat Tivon (IL); Vitaly Kuperman, Maalot (IL); Neta Sherer, Kibbutz Megido (IL)

(73) Assignee: ADASKY, LTD., Yokneam Illit (IL)

( * ) Notice: Subject to any disclaimer, the term of this patent is extended or adjusted under 35 U.S.C. 154(b) by 0 days.

(21) Appl. No.: 17/024,057

(22) Filed: Sep. 17, 2020

(65) Prior Publication Data
US 2022/0086370 A1    Mar. 17, 2022

(51) Int. Cl.
*H04N 5/33* (2023.01)
*G06T 7/80* (2017.01)
(Continued)

(52) U.S. Cl.
CPC ............. *H04N 5/33* (2013.01); *A61B 5/0075* (2013.01); *A61B 5/0077* (2013.01); *A61B 5/01* (2013.01);
(Continued)

(58) Field of Classification Search
CPC ........... H04N 5/33; F01D 5/28; F01D 25/005; F01D 25/00
See application file for complete search history.

(56) References Cited

U.S. PATENT DOCUMENTS

| 5,173,443 A | 12/1992 | Biricik et al. |
| 5,178,464 A | 1/1993 | Fraden |

(Continued)

FOREIGN PATENT DOCUMENTS

| CN | 204031303 U | 12/2014 |
| CN | 205175557 U | 4/2016 |

(Continued)

OTHER PUBLICATIONS

Donlon, et. al., "The Calibration and Intercalibration of Sea-Going Infrared Radiometer Systems Using a Low Cost Blackbody Cavity" Journal of Atmospheric and Oceanic Technology, vol. 16, Issue 9, Sep. 1999.

(Continued)

*Primary Examiner* — Md N Haque
(74) *Attorney, Agent, or Firm* — M&B IP Analysts, LLC (57) ABSTRACT

A radiometric camera having internal black body components and a method for calibrating a radiometric camera having internal black body components. A radiometric camera includes a detector, the detector further including a thermal detector configured to capture thermal images, wherein the thermal detector is pointed in a direction, wherein the radiometric camera is adapted to receive at least one black body element in front of the detector with respect to the direction of the thermal detector, the thermal detector having a plurality of portions including at least one first portion, wherein the at least one black body element affects radiation readings by the at least one first portion of a plurality of portions of the thermal detector when disposed in the radiometric camera.

24 Claims, 9 Drawing Sheets

(51) Int. Cl.
*A61B 5/01* (2006.01)
*A61B 5/00* (2006.01)

(52) U.S. Cl.
CPC ............... *A61B 5/41* (2013.01); *G06T 7/80* (2017.01); *A61B 2560/0223* (2013.01); *G06T 2207/10048* (2013.01); *G06T 2207/30196* (2013.01)

(56) References Cited

U.S. PATENT DOCUMENTS

| | | | |
|---|---|---|---|
| 5,414,439 | A | 5/1995 | Groves et al. |
| 5,602,389 | A | 2/1997 | Kato et al. |
| 5,613,968 | A | 3/1997 | Lin |
| 6,559,447 | B2 | 5/2003 | Wood |
| 6,759,949 | B2 | 7/2004 | Miyahara |
| 7,297,938 | B2 | 11/2007 | Fauci et al. |
| 7,348,562 | B2 | 3/2008 | Irani |
| 7,402,802 | B1 | 7/2008 | Terre et al. |
| 7,422,365 | B2 | 9/2008 | Chamberlain et al. |
| 7,862,593 | B2 | 1/2011 | Clement et al. |
| 7,965,336 | B2 | 6/2011 | Bingle et al. |
| 8,373,757 | B1 | 2/2013 | Nguyen |
| 8,471,911 | B2 | 6/2013 | Kallhammer et al. |
| 8,581,982 | B1 | 11/2013 | Haley et al. |
| 8,663,106 | B2 | 3/2014 | Stivoric et al. |
| 8,743,207 | B2 | 6/2014 | Boulanger et al. |
| 8,759,717 | B2 | 6/2014 | Chamberlain |
| 8,791,878 | B2 | 7/2014 | Yamazaki et al. |
| 9,061,632 | B2 | 6/2015 | Toyofuku |
| 9,090,205 | B2 | 7/2015 | Nagaoka et al. |
| 9,377,363 | B2 | 6/2016 | Boulanger et al. |
| 9,555,736 | B2 | 1/2017 | Solar et al. |
| 10,175,112 | B1 | 1/2019 | Kuperman et al. |
| 10,591,358 | B2 | 3/2020 | Kuperman et al. |
| 10,666,880 | B2 | 5/2020 | Kuybeda et al. |
| 2002/0162963 | A1 | 11/2002 | Lannestedt et al. |
| 2003/0146199 | A1 | 8/2003 | Sol et al. |
| 2005/0205773 | A1* | 9/2005 | Fauci ............ G12B 13/00 250/252.1 |
| 2006/0171704 | A1 | 8/2006 | Bingle et al. |
| 2007/0216768 | A1 | 9/2007 | Smith et al. |
| 2008/0110254 | A1 | 5/2008 | Zhao et al. |
| 2008/0203079 | A1 | 8/2008 | Veerasamy et al. |
| 2009/0062859 | A1 | 3/2009 | Mahoney et al. |
| 2010/0237055 | A1 | 9/2010 | Rousseau et al. |
| 2012/0209332 | A1 | 8/2012 | Janowski |
| 2013/0062228 | A1 | 3/2013 | Danilov |
| 2013/0235163 | A1* | 9/2013 | Joo ............ G03B 35/08 348/47 |
| 2014/0027433 | A1 | 1/2014 | Lisinski et al. |
| 2014/0092257 | A1 | 4/2014 | Hogasten et al. |
| 2014/0098238 | A1 | 4/2014 | Boulanger et al. |
| 2016/0075211 | A1 | 3/2016 | Kim |
| 2016/0203280 | A1 | 7/2016 | Neville |
| 2016/0334284 | A1 | 11/2016 | Mucharrafille et al. |
| 2016/0363483 | A1* | 12/2016 | Tzvieli ............ A61B 5/0075 |
| 2017/0374298 | A1* | 12/2017 | Teich ............ G01J 5/0846 |
| 2019/0132907 | A1 | 5/2019 | Kuperman et al. |

FOREIGN PATENT DOCUMENTS

| | | | | |
|---|---|---|---|---|
| CN | 108562363 | B | | 12/2019 |
| DE | 102007042268 | A1 | | 3/2009 |
| EP | 0872718 | A2 | * | 10/1998 |
| JP | 2004104632 | A | | 4/2004 |
| JP | 4604033 | B2 | | 12/2010 |
| JP | 2014032337 | A | | 2/2014 |
| KR | 100881713 | B1 | | 2/2009 |
| RU | 194363 | A1 | | 2/2006 |
| WO | 2004047421 | A2 | | 6/2004 |
| WO | 2010089627 | A1 | | 8/2010 |
| WO | 2014106276 | A2 | | 7/2014 |
| WO | WO-2014152681 | A2 | * | 9/2014 ............ G01J 5/025 |

OTHER PUBLICATIONS

Germanium window, ø 25.4 mm x 3.0 mm, Del Mar Photonics, San Diego, CA., URL: http://www.dmphotonics.com/Germanium-Optics/Germanium%20Windows%20and%20Lenses%20for%20Thermography.htm.

Germanium Windows with AR and DLC Coatings, Del Mar Photonics, Nov. 2012, URL: https://www.youtube.com/watch?v=Chg9SWcJNLw.

Germanium Windows/Substrates, Electro Optical Components, Inc., 2017, URL: http://www.eoc-inc.com/germanium_windows.htm.

Gomes, et.al., "Uncooled Thermal Camera Calibration and Optimization of the Photogrammetry Process for UAV Applications in Agriculture", MDPI-Sensors 2017, 17,2173.

Hartmann, et. al., "Calibration and Investigation of Infrared Camera Systems Applying Blackbody Radiation", Proceedings of SPIE, vol. 4360, 2001.

International Search Report and Written Opinion of International Searching Authority for PCT/US2018/067722, ISA/RU, Moscow, Russia, dated May 7, 2019.

Kusnierek, et. al., "Challenges in Using An Analog Uncooled Microbolometer Thermal Camera to Measure Crop Temperature" The International Journal of Agriculture and Engineering, vol. 7, No. 4, Aug. 2014.

Lane, et al., "Calibration and Measurement Procedures for a High Magnification Thermal Camera", National Institute of Standards and Technology, Gaithersburg, MD, 20899-8223.

Notice of Deficiencies for European Patent Application No. 18212592.2, Apr. 16, 2020, EPO, Munich, Germany.

Sosnowski, et. al.,"The Calibration Stand for Thermal Camera Module with Cooled Infrared Focal Plane Array", Infrared Technology and Applications XXXVI, Proceedings vol. 7660, 2010.

The First Chinese Office Action for Chinese Patent Application No. 2018115256038, dated Dec. 16, 2019, CNIPA, China.

The Second Chinese Office Action for Chinese Patent Application No. 2018115256038, dated Jul. 6, 2020, CNIPA, China.

Torres, et. al., "Limitations of a Thermal Camera in Measuring Surface Temperature of Laser-Irradiated Tissues" Wiley Online Library: Lasers in Surgery and Medicine, vol. 10, Issue 6.

\* cited by examiner

RADIOMETRIC CAMERA WITH BLACK BODY ELEMENTS FOR SCREENING INFECTIOUS DISEASE CARRIERS AND METHOD FOR CALIBRATING A THERMAL CAMERA HAVING INTERNAL BLACK BODY ELEMENTS

TECHNICAL FIELD

The present disclosure relates generally to thermal cameras usable in early diagnosis of infectious diseases, and more specifically to infrared cameras configured for calibration via inclusion of an internal black body.

BACKGROUND

Infectious diseases, such as influenza (flu) or the 2019 novel strain of coronavirus (COVID-19), are caused by viruses. In 2019, the entire world began experiencing the worst pandemic since the 1918 influenza pandemic. To control this pandemic and avoid future outbreaks, new methods and devices are needed to allow early detection and containment of potentially infected people that pose a high risk of transmitting diseases to others.

Screening for people carrying infectious diseases is critical in places with high densities of people such as airports, shopping centers, schools, hospitals, and the like. Thus, in order to prevent high-risk exposures, detection devices are required to screen high volumes of objects (people) in high-traffic areas in real time and with high precision.

One of the symptoms of infectious disease is a high body temperature. To this end, existing solutions for measuring human body temperatures in crowded areas are based on thermal cameras. Uncooled Bolometric thermal infrared (IR) cameras capture image wavelengths in the range of approximately seven to fourteen micrometers, also known as the long-wave infrared (LWIR) spectrum band. A typical IR camera uses an infrared sensor to detect infrared energy that is guided to the sensor through the camera's lens.

When implementing thermal measurements to obtain body temperature, there is a technical challenge of calibrating the camera to achieve accurate measurements. Some existing solutions suggest using calibrations based on an external black body. Such an external black body provides a thermal point of reference to the measurement.

A black body at thermal equilibrium (a constant temperature) emits electromagnetic radiation called black body radiation. The radiation has a spectrum that is determined by temperature alone. An ideal black body in thermal equilibrium has two notable properties: those of an ideal emitter and of a diffuse emitter.

To achieve higher accuracy, existing solutions require a number of black bodies. That is, the camera needs to be installed together with the black bodies on site. This requires adjusting and calibrating the location of the black bodies with respect to the camera, as well as waiting for all the involved temperature sources to stabilize. As such, implementing these solutions complicates the operation of the camera and increases the cost.

Further existing solutions utilize external black bodies. In other words, black bodies that are deployed outside of the camera. These solutions face challenges with increased cost and form factor. As a result of the increased form factor, these solutions may also face challenges with portability.

It would therefore be advantageous to provide a solution to overcome the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "certain embodiments" may be used herein to refer to a single embodiment or multiple embodiments of the disclosure.

Certain embodiments disclosed herein include a radiometric camera. The radiometric camera comprises: a detector, the detector further comprising a thermal detector configured to capture thermal images, wherein the thermal detector is pointed in a direction, wherein the radiometric camera is adapted to receive at least one black body element in front of the detector with respect to the direction of the thermal detector, the thermal detector having a plurality of portions including at least one first portion, wherein the at least one black body element affects radiation readings by the at least one first portion of a plurality of portions of the thermal detector when disposed in the radiometric camera.

Certain embodiments disclosed herein also include a method for calibrating a radiometric camera having internal black body components. The method comprises: comparing at least one first portion of an infrared image captured by a radiometric camera with at least one second portion of the infrared image, the radiometric camera including an infrared sensor having a plurality of portions including at least one first portion and at least one second portion, wherein the infrared sensor is pointed in a direction, wherein the radiometric camera is adapted to receive at least one black body element in front of the detector with respect to the direction of the infrared sensor, wherein the at least one black body element blocks radiation to the at least one first portion of the infrared sensor, wherein the at least one black body element does not block radiation to the at least one second portion of the infrared sensor, wherein the at least one first portion of the infrared image is captured by the at least one first portion of the infrared sensor, wherein the at least one second portion of the infrared image is captured by the at least one second portion of the infrared sensor, wherein the infrared image is captured by the infrared sensor when the at least one black body element is disposed in front of the detector; determining a plurality of calibration parameters for the infrared sensor based on the comparison, wherein each of the plurality of calibration parameters corresponds to one of the plurality of portions of the infrared sensor; and creating a calibration table, wherein the calibration table includes the plurality of calibration parameters for the plurality of portions of the infrared sensor, wherein the calibration table and the plurality of calibration parameters adjust for bias of the infrared sensor when utilized for calibrating the radiometric camera.

Certain embodiments disclosed herein also include a non-transitory computer readable medium having stored thereon instructions for causing a processing circuitry to perform a process, the process comprising: comparing at least one first portion of an infrared image captured by a radiometric camera with at least one second portion of the infrared image, the radiometric camera including an infrared sensor having a plurality of portions including at least one first portion and at least one second portion, wherein the infrared sensor is pointed in a direction, wherein the radiometric camera is adapted to receive at least one black body element in front of the detector with respect to the direction of the infrared sensor, wherein the at least one black body element blocks radiation to the at least one first portion of the infrared sensor, wherein the at least one black body element does not block radiation to the at least one second portion of the infrared sensor, wherein the at least one first portion of the infrared image is captured by the at least one first portion of the infrared sensor, wherein the at least one second portion of the infrared image is captured by the at least one second portion of the infrared sensor, wherein the infrared image is captured by the infrared sensor when the at least one black body element is disposed in front of the detector; determining a plurality of calibration parameters for the infrared sensor based on the comparison, wherein each of the plurality of calibration parameters corresponds to one of the plurality of portions of the infrared sensor; and creating a calibration table, wherein the calibration table includes the plurality of calibration parameters for the plurality of portions of the infrared sensor, wherein the calibration table and the plurality of calibration parameters adjust for bias of the infrared sensor when utilized for calibrating the radiometric camera.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

It has been identified that existing solutions face challenges in calibrating radiometric cameras generally, and more specifically face challenges in effectively utilizing external black bodies in calibration.

It has further been identified that existing radiometric camera structures are not suitably designed for insertion of an internal black body. Accordingly, the disclosed embodiments provide an improved radiometric camera structure which allows for insertion of a black body into the radiometric camera and techniques for calibrating the radiometric camera using the internal black body. The radiometric camera and calibration techniques described herein may be utilized to detect symptoms of infectious diseases as described herein.

In accordance with the disclosed embodiments, radiometric camera which is adapted for receiving black body elements is provided. The black body elements are disposed with respect to a detector portion of the infrared camera such that the black body elements affect radiation readings by an infrared sensor of the radiometric camera. To this end, the black body elements may be affixed to a lens of the radiometric camera, inserted between the lens and the window, or affixed or otherwise disposed on a side of the window such that the black body elements partially cover a detector window opening as described herein.

In an embodiment, when the black body elements are affixed to an outer side of the lens of the camera, the black body affects radiation readings by the infrared sensor of the camera by irradiating patterns which affect pixels of images captured by the detector rather than blocking portions of the detector in order to affect the pixels of the images captured by the detector. In such an embodiment, calibrating the camera includes separating the pattern as shown in an infrared image from the image itself via image processing. The pattern may then be utilized to determine a temperature of the black body, which in turn is used for calibration.

In another embodiment, when the black body elements are not affixed to the outer side of the lens (e.g., when the black body elements are inserted between the lens and the protective window, affixed to the window, or otherwise disposed on the window), the black body affects radiation readings by the infrared sensor of the camera by blocking radiation that would be detected by one or more first portions of the infrared sensor and does not block one or more second portions of the infrared sensor. The black body elements therefore affect the second portions of the infrared sensor but have a significantly reduced influence thereon as compared to effect on the first portions.

By deploying the black body elements inside of the disclosed radiometric camera, the disclosed embodiments allow for calibrating readings of the radiometric camera via comparison of readings from portions of the detector blocked by the black body elements with readings from portions of the detector not blocked by the black body elements. The black body elements may be positioned at a predetermined location relative to the detector such that a distance between the detector and the black body elements may be known without requiring a user of the radiometric to provide or measure such distance. Additionally, since the black body elements are deployed inside of the radiometric camera, a heating element disposed inside the radiometric camera may be utilized to heat the black body to a given temperature. This allows for setting the black body elements to a known temperature required for calibration purposes without requiring a user of the radiometric camera to separately set such temperature or otherwise requiring additional heating components aside from the components of the radiometric camera. To this end, in a further embodiment, the black body elements may be heated to a predetermined temperature that approximates the normal temperature for a human (i.e., a temperature that would typically be detected for a human that is not experiencing elevated temperature due to, for example, fever). Alternatively or additionally, one or more temperature sensors may be deployed alongside the black body, thereby allowing for measuring the temperature of the black body directly.

The radiometric camera may be designed to provide simultaneous accurate body temperature measurements for multiple objects in a crowded area. In an example implementation, such objects include people. In an embodiment, the radiometric camera is calibrated using a black body inserted therein. The accurate measurements are achieved by correcting fixed pattern noises (FPNs) and determining a gamma drift reference. The gamma drift reference is the amount of drift during the camera operation.

In some embodiments, the black body elements may be included in the radiometric camera. In other embodiments, the radiometric camera may be adapted to allow for insertion of black body elements as described herein, and the black body elements may be provided by a user or manufacturer of the radiometric camera. The black body elements may be removed after calibration. In an example implementation, the black body elements may be inserted into the radiometric camera during calibration, and after calibration the radiometric camera may be provided to the user without including the black body elements.

Figure 1:
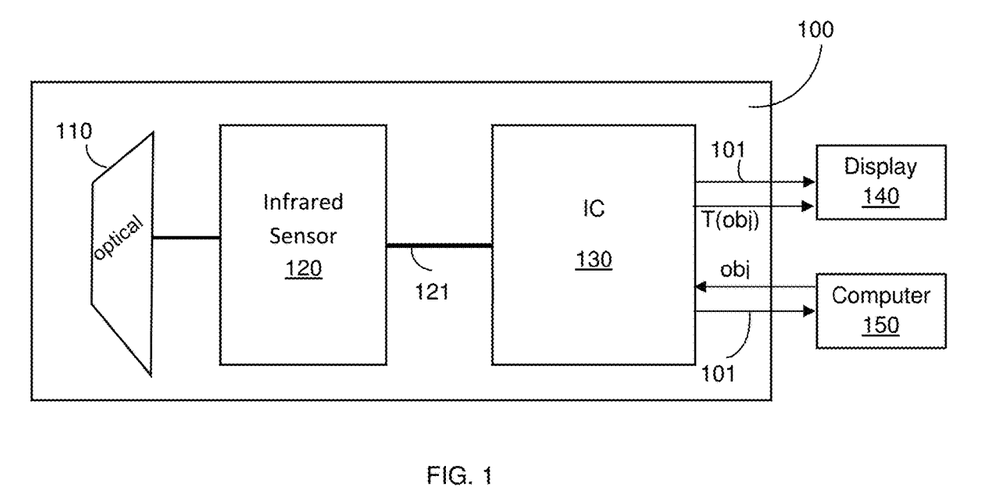
FIG. 1 shows a block diagram of a high throughput radiometric camera, utilized to describe the various disclosed embodiments.

FIG. 1 shows an example block diagram of a high throughput radiometric camera (hereinafter, the "camera 100") designed according to the various disclosed embodiments. More specifically, FIG. 1 illustrates components of the radiometric camera related to obtaining and processing sensor signals as well as providing outputs thereof.

The camera 100 includes an optical unit 110 and an infrared sensor 120 coupled to an integrated circuit (IC) 130. The output of the radiometric camera 100 is a video stream of thermal images (hereinafter a "thermal video stream") captured by the infrared sensor 120 and processed by the IC 130.

The thermal video stream is interposed with body temperature measurements and displayed together on a display 140. The display 140 may be external to the camera 100. In another embodiment, the display may be an LCD screen encapsulated in the same housing (not shown) of the camera 100. The body temperature measurements are presented with respect to each object identified in the thermal image. In an example implementation, the body temperature measurements may be presented using boxes around the object. The measurements may be presented as a numerical value, a color-coded indication, or both.

In an embodiment, the infrared sensor 120 is an uncooled long-wavelength infrared (LWIR) sensor, operating in a spectrum band of wavelengths of 7-14 μm. The spectrum of passive heat emission by a human body, predicted by Planck's law at 305 K, greatly overlaps with the LWIR spectrum band. Thus, high-resolution LWIR cameras and sensors are a good choice for designing high-throughput temperature screening solutions for human subjects. An uncooled sensor having a small form factor can typically be mass-produced using low-cost technology. The infrared sensor 120 includes, or is realized as, a focal plane array (FPA). An FPA produces a reference signal utilized to derive temperature information from the thermal image signal. In some configurations, the sensor 120 and the FPA (not shown) are the same unit and are collectively referred to hereinafter as the "infrared sensor 120."

The camera 100 outputs a thermal image stream 101 of denoised thermal images, fed into both a computer 150 and a display 140. As will be discussed below with reference to FIG. 2, to measure a temperature of an object, the IC 130 is configured to estimate the gamma drift offset and to subsequently neutralize the effect of changes in the sensor's 120 FPA temperature based on this drift so that normalized readings for different temperatures of the FPA can be recorded. The FPA temperature is the temperature in the vicinity of the FPA and sensor 120. The FPA temperature stabilization process results in a pixel response signal (Is). The IC 130 is further configured to determine the scene temperature value (Ts). The Ts value is used, in part, by a radiometric process that is also performed by the IC 130, to determine the temperature of objects in the scene (current denoised image).

In an embodiment, the IC 130 is further configured to calibrate the infrared sensor based on sensor signals reflecting both portions of a detector (not shown in FIG. 1) of the optical unit 110 that are blocked by a black body element and portions of the detector that are not blocked by a black body element as described further below.

The computer 150 is configured to perform at least a perception process. The perception process is configured to identify objects (e.g., persons) in input images. In an embodiment, the identified object is a person and the measured temperature is a human body temperature. The computer 150 may receive environmental data related to, for example, an ambient temperature, a current measured room (e.g., an office), temperature, humidity information, and the like. To this end, the computer 150 may interface with HVAC controllers, wireless thermostats, and the like. Such data may be provided to the camera 100 to be utilized in the radiometry process.

The computer 150 may be any computing device or unit including a processing circuitry (not shown) coupled to a memory (not shown), an input/output (I/O) interface (not shown), and a network interface (not shown). The processing circuitry may be realized as one or more hardware logic components and circuits. For example, and without limitation, illustrative types of hardware logic components that can be used include field programmable gate arrays (FPGAs), application-specific integrated circuits (ASICs), application-specific standard products (ASSPs), system-on-a-chip systems (SoCs), general-purpose microprocessors, microcontrollers, digital signal processors (DSPs), and the like, or any other hardware logic components that can perform calculations or other manipulations of information. The memory may be, for example, a flash memory, or any type of non-volatile memory.

In an embodiment, the perception and radiometry processes may be implemented or performed by the IC 130. Thus, in such configurations, the computer 150 is not required. In another embodiment, the computer 150 and the camera 100 are part of a radiometric system.

In one configuration, the optical unit 110 includes one or more lens elements (not shown in FIG. 1), each of which having a predetermined field of view (FoV). In an embodiment, the lens elements may be made of chalcogenide.

In an example configuration, the infrared sensor 120 is coupled through a communication bus 121 to the IC 130 to allow for inputting the captured thermal images, metadata, and other control signals (e.g., clock, synchronization, and the like).

Figure 2:
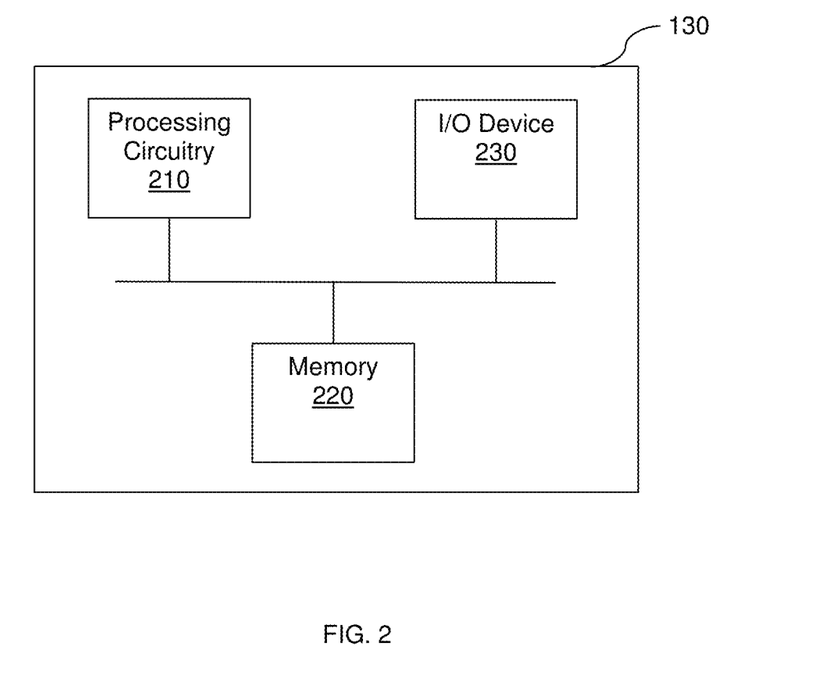
FIG. 2 shows a block diagram of an integrated circuit configured according to an embodiment.

The IC 130 includes a memory, a processing circuitry, and various circuits and modules allowing for executing the processes described herein. A detailed block diagram of the IC 130 is shown in FIG. 2. The IC 130 may be realized as a chipset, a system-on-a-chip (SoC), a field programmable gate array (FPGA), a programmable logic device (PLD), an application-specific integrated circuit (ASIC), or any other type of digital and/or analog hardware components.

According to the disclosed embodiments, the temperature measurements are performed without any external black body and without using a shutter as a reference point. Temperature measurements may be based, in part, on a gamma-based drift measurement algorithm that outputs the amount of drift during operation of the camera 100. An example gamma-based drift measurement algorithm is described in U.S. Pat. No. 10,511,793, assigned to the common assignee, the contents of which are hereby incorporated by reference. The changes in temperature of the infrared sensor 120 creates offsets that may be different from pixel to pixel. Therefore, in addition to a common drift component (DC), there is a fixed pattern noise that is added to each image. In an embodiment, the IC 130 is configured to measure the fixed-noise pattern during calibration of the camera 100 and to estimate the amount of the gamma drift during operation.

In an example implementation, the camera 100 is calibrated during manufacturing (e.g., at a lab) prior to operation. The calibration process is performed to stabilize the camera 100 at a predefined temperature. The calibration process includes reading the ambient temperature, which is periodically read from the sensor 120 to determine temperature stability, as well as comparing portions of an infrared image in which a first portion is captured by a part of a detector that is blocked by black body elements and a second portion is captured by a part of a detector that is not blocked by black body elements.

In an example configuration, the sensor 120 and IC 130 are encapsulated in a thermal core (not shown). The thermal core is utilized to ensure a uniform temperature for the camera 100. The temperature calibration of the thermal core is also factory calibration. The optical unit 110 is typically assembled in the camera 100 after the infrared sensor 120 and IC 130 are encapsulated in the thermal core.

As will be discussed below, the processing performed by the IC 130 enhances the quality of the captured thermal images to allow for the accurate and fast detection of objects (e.g., persons). To this end, the IC 130 may be configured to perform one or more image processing tasks, such as shutterless correction of the captured thermal images and correction of fixed pattern noise due to ambient drift. As demonstrated in FIG. 1, the camera 100 does not include a shutter (or any moving part that can be viewed as shutter). To this end, the IC 130 may be configured to execute shutterless image correction for the performance of a flat-field correction without a shutter. That is, shutterless correction allows for a radiometry image with unwanted fixed pattern noise removed therefrom.

In another embodiment, the camera 100 includes a shutter (or any equivalent moving part). Using a shutter can allow for improving noise reduction as may be required in static cameras as well as for increasing uniformity in the image-based temperature sensing.

The radiometric system including the radiometric camera 100, the display 140, and the computer 150, as illustrated in FIG. 1, may be utilized to provide early diagnosis system for infectious diseases such as, but not limited to, influenza, coronavirus, severe acute respiratory syndrome, and the like. One of the common symptoms of such diseases is elevated body temperature. Thus, by providing a system that can accurately measure body temperature, the disclosed embodiments allow for providing early detection of elevated body temperature, and thus indication of potential infection carriers. Furthermore, due to the ability of the radiometric camera 100 to measure temperature of many people simultaneously, the system can be installed in areas with high traffic of people such as airports, stadiums, train stations, and the like.

FIG. 2 shows an example block diagram of the IC 130 according to an embodiment. The IC 130 includes a processing circuitry 210, a memory 220, and an input/output (I/O) device 230.

The processing circuitry 210 is configured to control the various elements of the IC 130. The processing circuitry 210 is further configured to power-up the infrared sensor (FIG. 1, 120) and to upload the initial calibration tables.

The processing circuitry 210 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

In an embodiment, the memory 220 is configured to store calibration tables. The calibration tables include calibration values for each pixel computed in the lab. The calibration values may include gain and offset values calculated from two temperature points ($T_1$, $T_2$) for the purpose of overcoming the irregularities in the infrared sensor (120, FIG. 1) and unifying the pixels' response to infrared radiation for a normal ambient room temperature. The calibration tables also include a drift value determined for each pixel at a room temperature point during the calibration process. In an embodiment, the calibration tables also store various parameter values which may be applied to set the radiometric camera 100.

The memory 220 may further store computer readable instructions to be executed by the processing circuitry 210 and by the circuits 220, 230, 240, and 250. Computer readable instructions shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry and circuits, cause these processors to perform the various embodiments and tasks described herein. The memory 215 may be volatile (e.g., RAM, etc.), non-volatile (e.g., ROM, flash memory, etc.), or a combination thereof.

The IC 130 interfaces with the external elements (e.g., the infrared sensor 120, the display 140, and the computer 150, FIG. 1) via the I/O device 230. The I/O device 230 may be, but is not limited to, a multimedia link (not shown). In an example implementation, the multimedia link is a gigabit multimedia serial link (GMSL).

Figure 3:
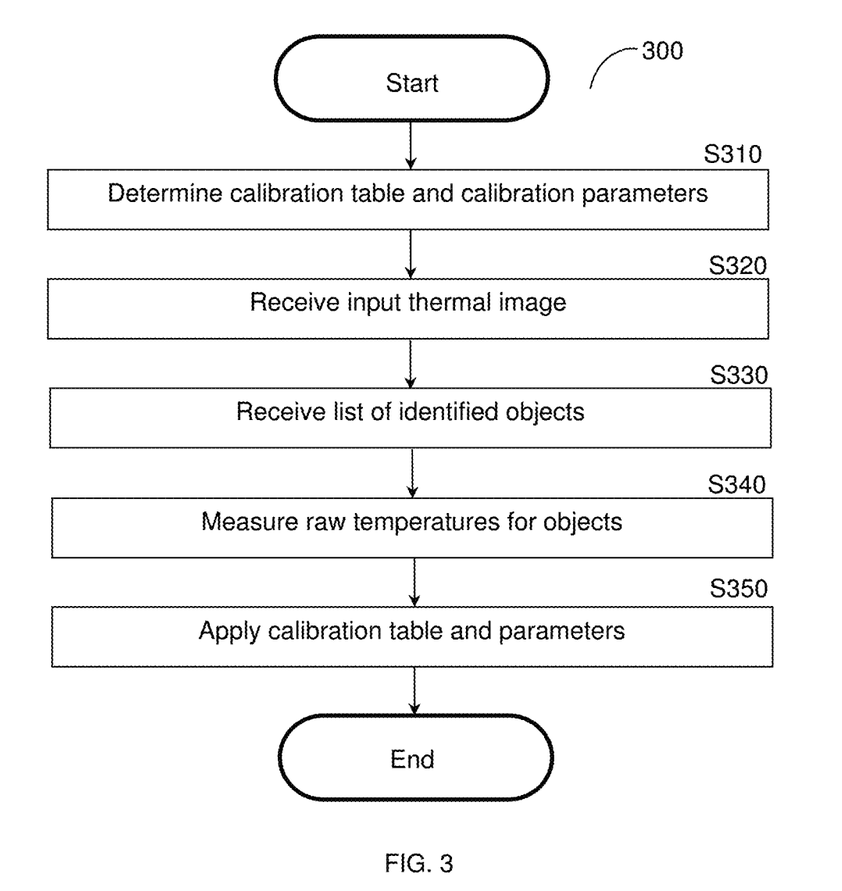
FIG. 3 shows a flowchart illustrating a method for obtaining accurate radiometric readings using a radiometric camera calibrated with an internal black body.

FIG. 3 is an example flowchart 300 illustrating a method for obtaining accurate radiometric readings using a radiometric camera calibrated with an internal black body according to an embodiment.

At S310, a calibration table is obtained. In an embodiment, the calibration table includes calibration parameters for each pixel of the infrared sensor. For example, the calibration parameters may represent the amount of anticipated gain (G), offset (O), and drift (D) associated with each portion of a radiometric camera (e.g., the portions of the sensor responsible for each pixel in infrared images captured by the radiometric camera). The calibration table and parameters may be stored in a memory or database that is remotely or locally accessible.

In an embodiment, the calibration table is created using a calibration process including comparing different portions of thermal images. More specifically, a detector of a radiometric camera is partially blocked by black body elements as described herein such that a first portion of each image captured by the radiometric camera during calibration acts as a control portion due to absorption of radiation by the black body elements and a second portion of each image acts as a test portion with radiation that is not absorbed by the black body. Example configurations for the radiometric camera during calibration are described further below with respect to FIGS. 5A-D, and an example method for calibrating such a radiometric camera is described further below with respect to FIG. 6.

At S320, a thermal image is received from the infrared sensor, e.g., the sensor 120 of FIG. 1, above.

At S330, a list of objects identified in the denoised thermal image, together with the distance of each object from the camera, is received.

At S340, raw temperatures for the identified objects are determined. The raw temperatures are determined based on the input thermal image. An object temperature is measured independently of the ambient temperature of the camera.

At S350, the calibration table is applied to the measured raw temperatures in order to accurately determine the temperatures of the identified objects in the input thermal image.

In an example implementation, the measured object temperatures are used to label the input thermal image such that the measured object temperatures are displayed next to each respective object overlaid in the image when the thermal image is provided for display on, for example, a user device.

It should be noted that the embodiments described with respect to FIG. 3 as including determining a calibration table and calibration parameters in the same process as applying those calibration table and calibration parameters to an input thermal image, but that the disclosed embodiments do not require performing these steps around the same time. In an example implementation, the calibration table and calibration parameters are determined prior to the other steps, for example days or weeks in advance. As non-limiting examples, the calibration table and calibration parameters may be determined at the manufacturer's facility prior to being shipped for use, or the table and parameters may be determined upon receipt by a user of the radiometric camera but prior to measuring temperatures.

Figure 4:
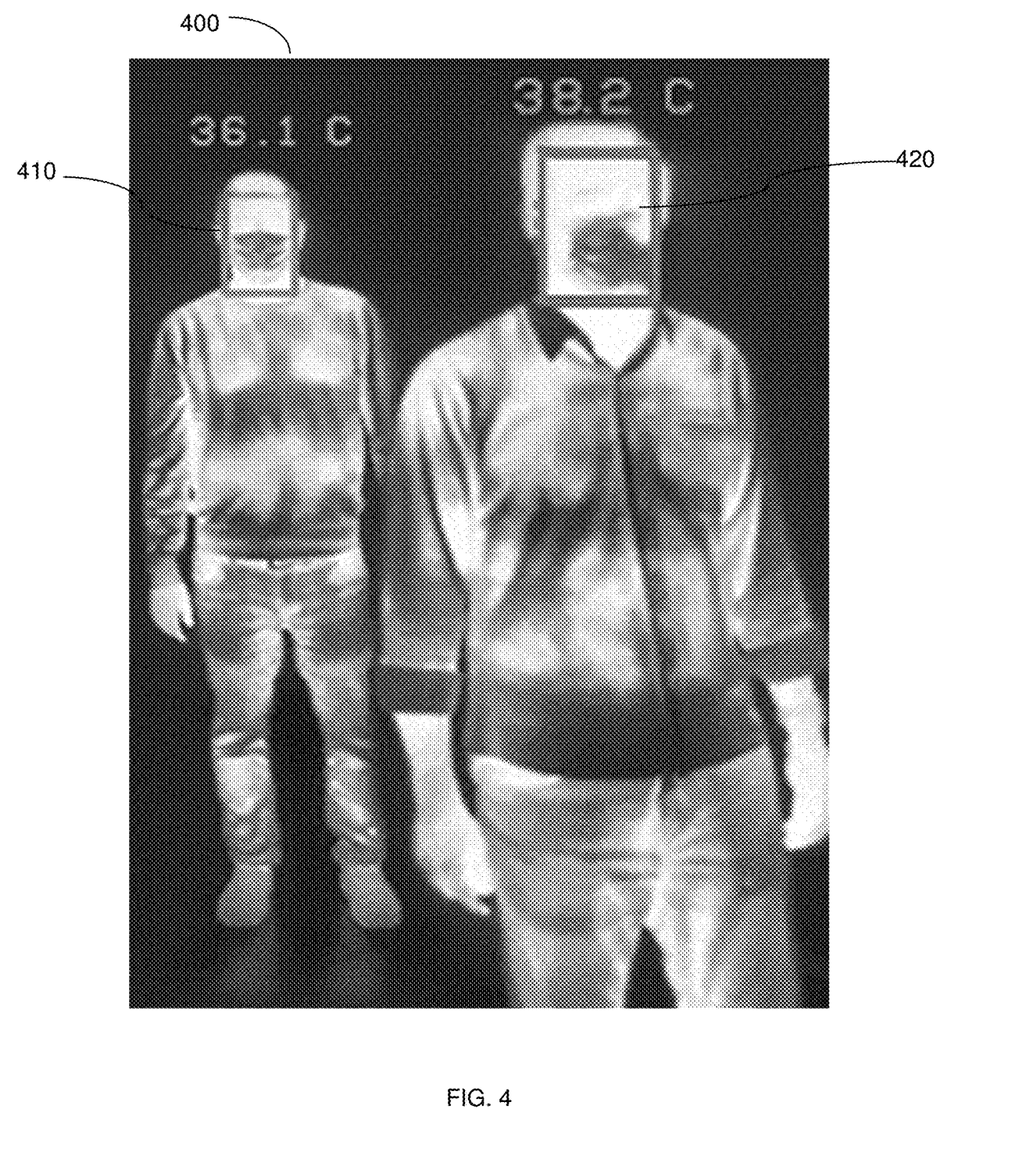
FIG. 4 shows an example output denoised image, applicable to identify objects.

FIG. 4 shows an example output denoised image 400 used to identify persons (objects) 410 and 420. In the example image 400, a respective temperature is displayed next to each person 410 or 420. The displayed temperature may be color-coded, for example, the person 420 may be boxed with a red box, while the person 410 may be boxed with a green box.

FIGS. 5A-D are example schematic diagrams of respective radiometric cameras 500A through 500D having distinct configurations. More specifically, each of FIGS. 5A-D illustrates a distinct configuration of a radiometric camera with black body elements disposed therein. FIGS. 5-D illustrate components related to the mechanical structure of the respective radiometric cameras 500A through 500D which are utilized to explain the deployment of the black body elements as described herein. The black body elements are disposed with respect to a detector such that the black body elements block radiation from a portion of images captured by the detector.

In FIGS. 5A-D, a respective radiometric camera 500A through 500D includes at least a lens 510, a sensor window 520, a detector 530, and black body elements 540-1 and 540-2 (hereinafter referred to as black body elements 540 for simplicity).

The detector 530 includes the sensor elements that allow for capturing thermal images and may be, but is not limited to, a focal plane array. The black body elements 540 are deployed in front of the detector 530, i.e., in the direction that the detector 530 is facing, and partially block radiation that would otherwise be detected by the detector 530. As a result, images captured by the detector 530 while the black body elements 540 are disposed in one of the radiometric cameras 500A through 500D include one or more first portions for which radiation is blocked by the black body elements 540, and one or more second portions for which radiation is not blocked by the black body elements 540.

In the example configurations shown in FIGS. 5A-D, the detector 530 is pointing leftward. The window 520 is therefore disposed in front of the detector 530 and the lens 510 is disposed in front of the window 520, wherein "in front of" is defined relative to the direction the detector 530 is facing. In all of the configurations, the black body elements 540 are disposed in front of the detector 530, but may be disposed in various locations relative to other parts of the respective radiometric cameras 500A through 500D.

Figure 5A:
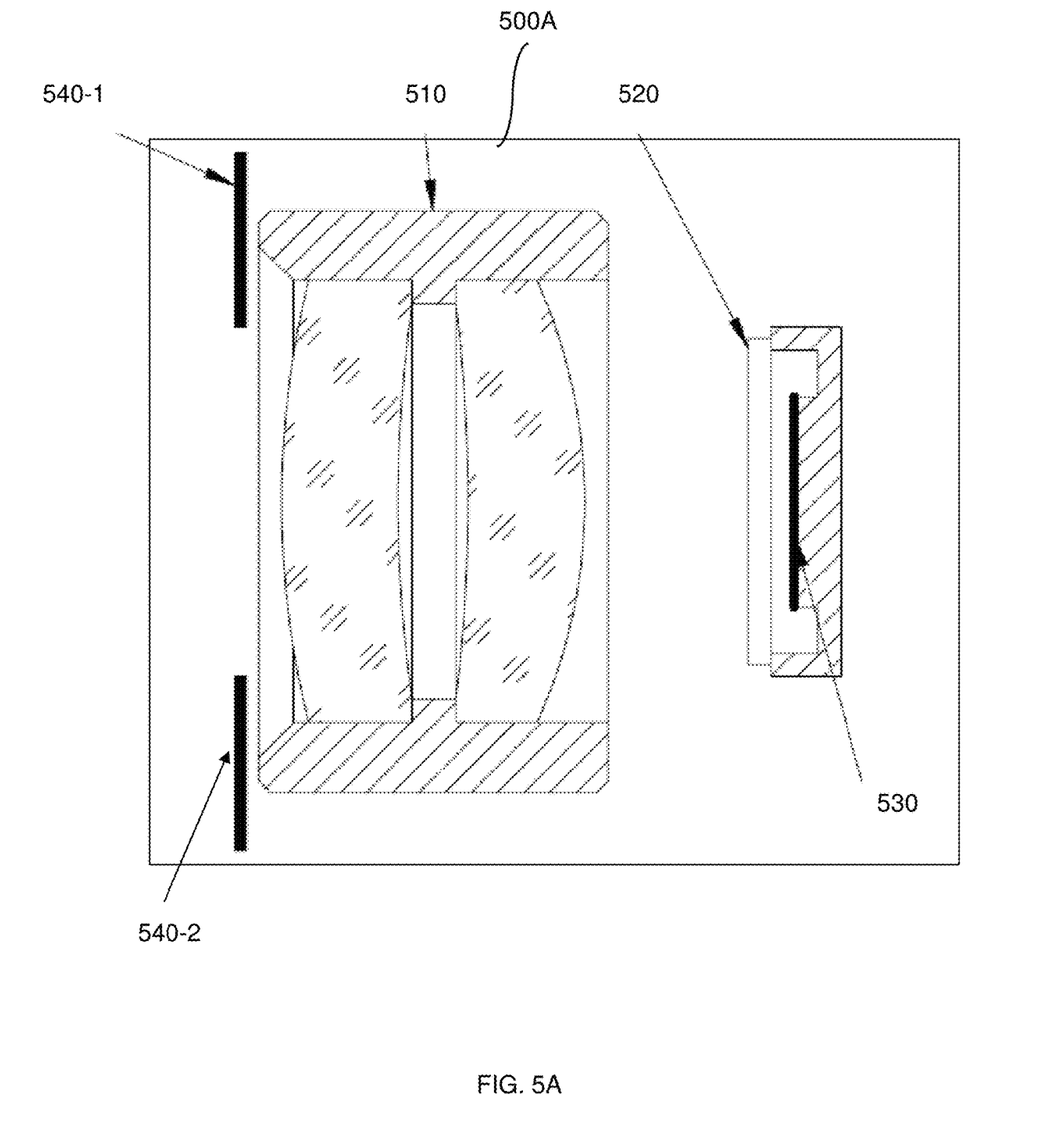
FIGS. 5A-D are schematic diagrams illustrating a radiometric camera including a black body according to various embodiments.
Figure 5B:
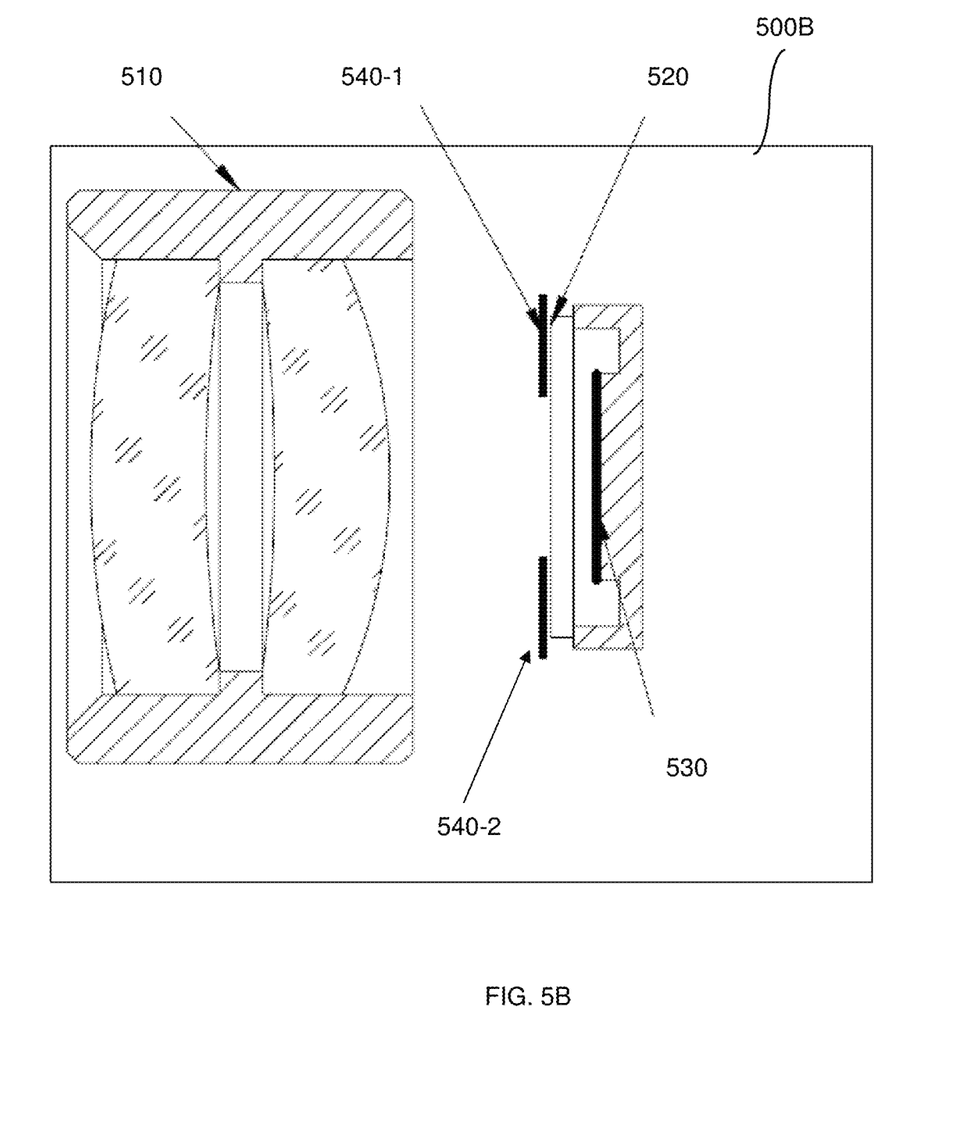
Figure 5C:
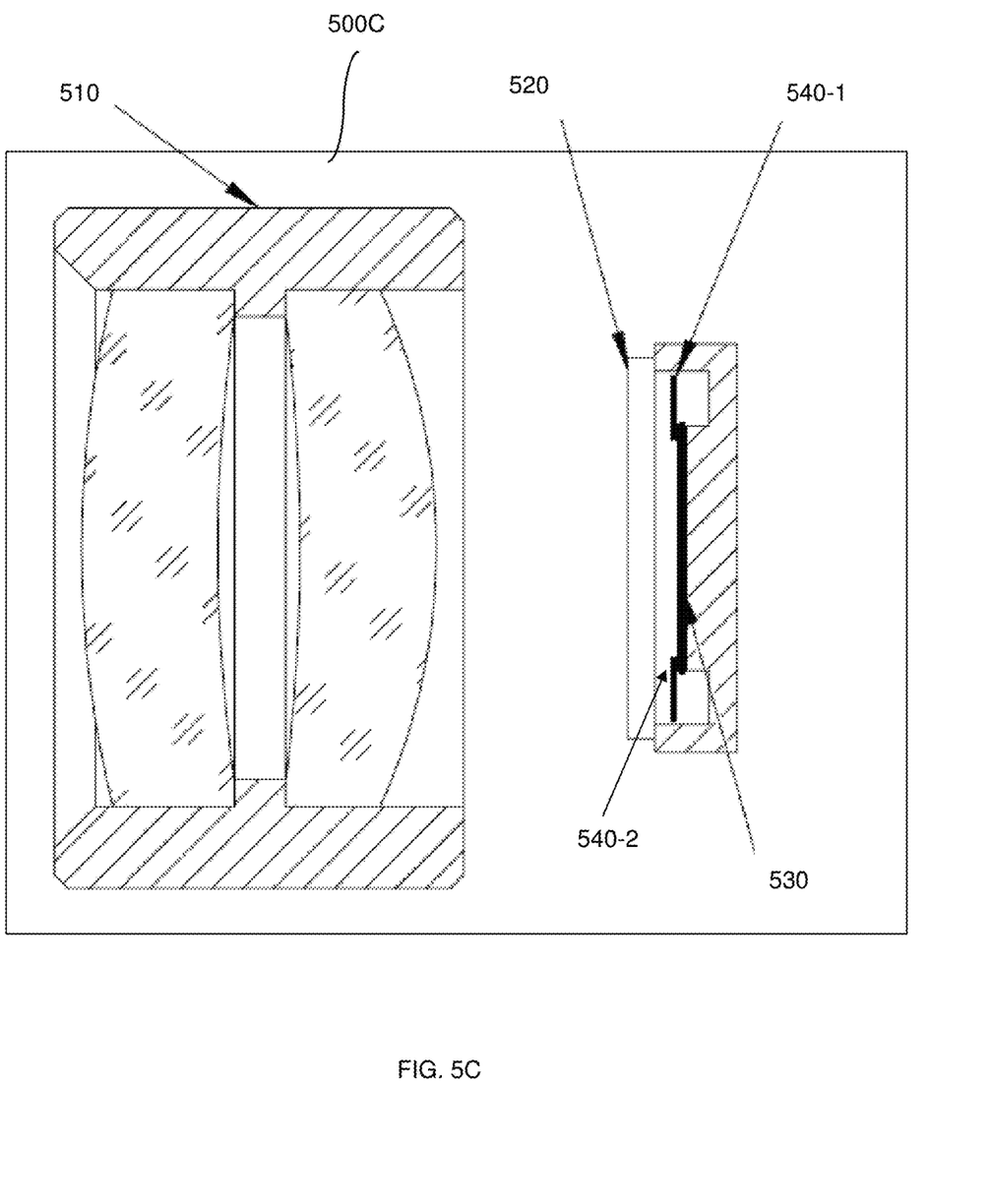

FIG. 5A illustrates a schematic diagram 500A in which the black body elements 540 are disposed in front of the lens 510. In this implementation, the black body elements 540 irradiate patterns on the detector 530 such that radiation readings by portions of the infrared sensor (not shown) of the detector 530 are altered. FIG. 5B illustrates a schematic diagram 500B in which the black body elements 540-1 and 540-2 are disposed between the lens 510 and the window 520. In FIG. 5B, the black body elements 540 are shown as immediately adjacent to the window 520, but in other configurations the black body elements 540 may be further separated to the window 520. FIG. 5C illustrates a schematic diagram 500C in which the black body elements 540 are disposed between the window 520 and the detector 530. In the example implementations shown in FIG. 5B-C, the black body elements 540 may block portions of the detector 530 such that radiation readings by portions of the infrared sensor (not shown) of the detector 530 are altered.

Figure 5D:
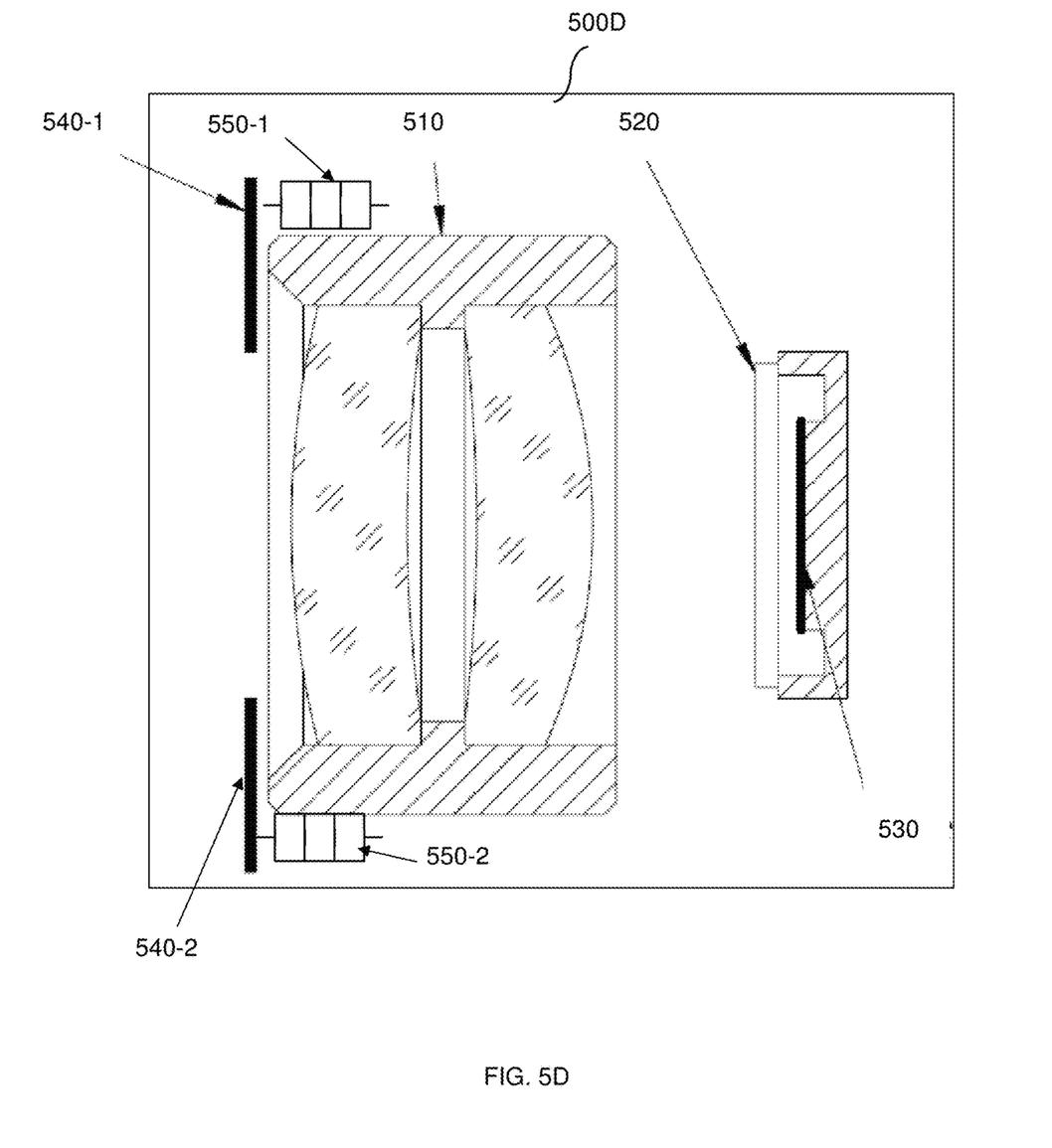

FIG. 5D illustrates an example schematic diagram of a radiometric camera 500D further including heating elements 550-1 and 550-2 (referred to as heating elements 550 for simplicity). Each of the heating elements 550 is configured to heat one or more of the black body elements 540 in order to set the respective black body elements 540 at a given temperature as used for calibration, for example, as described further below with respect to FIG. 6.

In some embodiments, the window 520 may be configured for resistive heating, for example, as described further in U.S. patent application Ser. No. 15/799,436, assigned to the common assignee, the contents of which are hereby incorporated by reference. To this end, the window 520 may include a low conductivity transparent member and one or more sets of conductive pads (not shown) such that running an electrical current through the window 520 causes the window to become heated. The conductivity of the member may be, for example, below a threshold. The transparency of the member is at least with respect to the long wavelength infrared (LWIR) spectrum. The window 520 may be made of any suitable material such as, but not limited to, Germanium and, in particular, N-type Germanium.

The resistive heating window 520 can, in turn, be utilized to heat up black body elements 540 affixed to or otherwise adjacent to the window 520, for example as depicted in FIG. 5B. By utilizing a resistive heating window such as a window having the features described in the Ser. No. 15/799, 436 application, the black body may be heated without requiring integrating a dedicated heating element in the radiometric camera.

It should be noted that FIGS. 5A-D are depicted as including two black body elements merely as an example, but that other numbers of black body elements may be equally utilized without departing from the scope of the disclosure.

Figure 6:
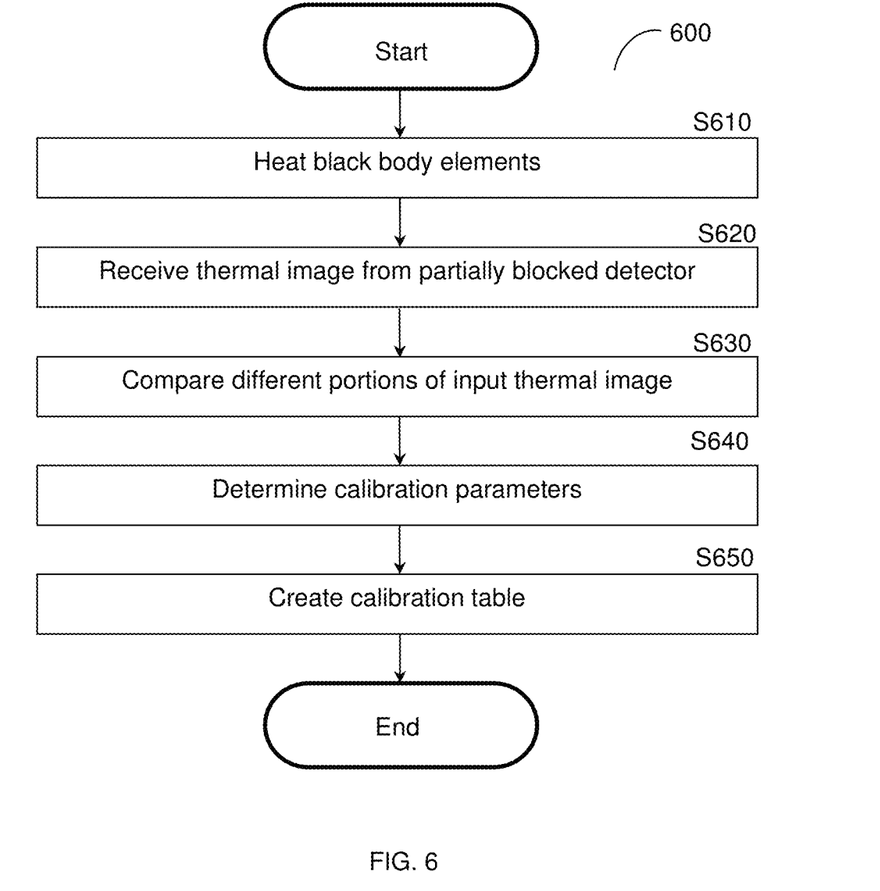
FIG. 6 is a flowchart illustrating a method for calibrating a radiometric camera having internal black body elements according to an embodiment.

FIG. 6 is an example flowchart 600 illustrating a method for calibrating a radiometric camera including black body elements according to an embodiment.

At optional S610, black body elements inside the radiometric camera are heated to a predetermined temperature. The heating may be performed, for example, using heating elements or a window configured for resistive heating as described further above with respect to FIG. 5D. The black body elements are therefore heated such that the actual temperature of the black body becomes equal or roughly equal (e.g., within a threshold) to the predetermined temperature.

The actual temperature of the black body elements may be received, for example, from a temperature sensor deployed alongside the black body elements. Such a temperature sensor may be attached to the black body elements and therefore provides temperature readings that represent the temperature of the black body elements.

At S620, a thermal image is received from a detector (e.g., the detector 530, FIGS. 5A-D) whose radiation readings are partially affected by the black body elements inside the radiometric camera. More specifically, the detector may include an infrared sensor having multiple portions, where readings by one or more first portions of the infrared sensor are affected by the black body and readings by one or more second portions of the infrared sensor are not affected by the black body. As a non-limiting example, each of the first and second portions may be a portion of the infrared sensor configured to capture a pixel of an infrared image collectively captured by the first and second portions.

In an embodiment, the black body elements partially block the infrared sensor of the detector such that the first portions of the infrared sensor are blocked and the second portions of the infrared sensor are not blocked. Because the detector is partially blocked by the black body elements, the thermal image includes one or more first portions corresponding to the blocked part of the detector's sensors and one or more second portions corresponding to the non-blocked part of the detector sensors. As a non-limiting example, a first portion of the thermal image may include a first set of pixels, and a second portion of the thermal image may include a second set of pixels.

In this regard, it has been identified that, while the second portions of the infrared sensor are not blocked by the black body elements directly, the black body elements may influence the readings of the otherwise unblocked second portions of the infrared sensor via stray radiation. When such influence occurs, calibrating the radiometric camera further requires adjusting the readings of the second portions of the infrared sensor accordingly. In some embodiments, the number of second portions of the infrared sensor may be sufficiently large such that the second portions capture both blocked and influenced radiation readings. In such embodiments, no correction of the thermal image is required.

In another embodiment, the black body elements are disposed on an outer surface of the lens of the camera such that the black body elements irradiate an out-of-focus black body pattern onto the focal plane array (FPA) of the infrared detector. More specifically, the irradiated pattern is superimposed on the first portions of the infrared sensor, and the irradiated pattern is not superimposed on the second portions of the infrared sensor. As a result, the black body elements create a superposition of out of focus and in focus portions of images based on the superimposed pattern. As a result, the difference may be identified via image processing and utilized to measure a temperature of any or each of the black body elements as described further below.

It should be noted that first and second portions of the infrared sensor are discussed with respect to different relative positions of the black body element, and that the first and second portions are not necessarily the same in different implementations. Which portions of the infrared sensor are affected by the black body elements and which portions are not affected by the black body elements may depend, for example, on the position and orientation of the black body elements. The differences are determined via comparison of thermal readings.

At S630, the first and second portions of the thermal image are compared to determine a difference in thermal readings.

At S640, based on the comparison, calibration parameters are determined. The calibration parameters may include, but are not limited to, calibrated values may represent the amount of anticipated gain (G), offset (O), and drift (D) associated with each pixel due to inherent biases of the radiometric camera.

In an embodiment, the calibration parameters are determined based further on a temperature measured for the black body elements. To this end, in such an embodiment, S640 further includes measuring the temperature of the black body elements. The temperature of the black body elements may be measured before, during, or after heating of the black body elements in order to allow for using the measured temperature to compensate for camera drift due to ambient temperature changes.

In an example implementation, the temperature of the internal black body elements is measured using the following equation.

$$T_O = G * I_U + O \qquad \text{Equation 1}$$

In Equation 1, $T_O$ is an temperature of an object, G is a gain that converts infrared sensor readings of the second portions to temperature units, $I_U$ is a response of the infrared sensor to object radiation in the unblocked second portions, and O is an offset that changes as the ambient temperature of the radiometric camera changes.

Because the offset O is variable, in the example implementation noted above with respect to Equation 1, the offset may be first estimated based on the temperature of the black body elements in accordance with the following equation.

$$O = T_{bb} - G * I_B \qquad \text{Equation 2}$$

In Equation 2, $T_{bb}$ is the temperature of the black body element (e.g., a temperature the black body was raised to via a heating element or a temperature determined via sensor readings from a temperature sensor deployed with the black body element). Since the black body elements can be located between the lenses and the detector, its influence, as seen by the detector, can be different compared to the influence of object radiation located behind the lenses (i.e., a lens transfer function and self-radiation can add a gain and offset). In an example implementation, $\hat{I}_B$ may be determined in accordance with the following equation.

$$\hat{I}_B = G_B * I_B + O_B \quad \text{Equation 3}$$

In Equation 3, $I_B$ is the response of the radiometric camera to radiation from the black body elements, and $G_B$ and $O_B$ are calibration parameters used to calibrate the response of the radiometric camera to the black body elements at a given temperature to match readings of the radiometric camera to external objects (e.g., humans) at the given temperature. The value of $I_B$ may be measured directly when the black body elements are disposed close to the detector (e.g., when the black body elements are disposed between the detector and a window of the camera or between the window and a lens of the camera), or may be estimated by analyzing a pattern projected by the black body elements when the black body elements are disposed farther away (e.g., when the black body elements are disposed in front of a lens of the camera).

The calibration parameters $G_B$ and $O_B$ may be determined, for example, during manufacturing, separately for different ranges of ambient temperature or different distances to external objects, thereby allowing for determining different sets of calibration parameters for different circumstances.

In an example implementation, $I_B$ may be determined as an average of sensor reading values from the first portions of the infrared sensor that are blocked by the black body elements. Such an implementation may be appropriate when, for example, the black body elements are disposed relatively close to the detector including the infrared sensor. When the black body elements are relatively far away (e.g., when the black body elements are deployed in or near an outer surface of a lens of the radiometric camera), a more complex function may be applied to the sensor readings based on the pattern, which will also influence the value of calibration parameters $G_B$ and $O_B$.

The offset value O may then be substituted back into Equation 1, thereby resulting in the following new equation for determining the temperature of an object.

$$T_O = G^*(I_U - \hat{I}_B) + T_{bb} \quad \text{Equation 4}$$

Equation 4 therefore provides cancellation of any drifting offset caused by changes in ambient temperature based on known or measured values for the temperature of the black body elements and the readings from the blocked portions of the infrared sensor, thereby improving accuracy of the object temperature measurements by the radiometric camera.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform, such as an additional data storage unit and a printing unit. Furthermore, a non-transitory computer readable medium is any computer readable medium except for a transitory propagating signal.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; A and B in combination; B and C in combination; A and C in combination; or A, B, and C in combination.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A radiometric camera, comprising:
   a detector, the detector further comprising a infrared sensor configured to capture thermal images, wherein the infrared sensor is pointed in a direction, wherein the radiometric camera is adapted to receive at least one black body element in front of the detector with respect to the direction of the infrared sensor, the infrared sensor having a plurality of portions including at least one first portion, wherein the at least one black body element affects radiation readings by the at least one first portion of a plurality of portions of the infrared sensor when disposed in the radiometric camera;
   a processing circuitry; and
   a memory, the memory containing instructions that, when executed by the processing circuitry, configure the processing circuitry to:
   compare at least one first portion of an infrared image captured by the infrared sensor with at least one second portion of the infrared image, wherein the at least one first portion of the infrared image is captured by the at least one first portion of the infrared sensor, wherein the at least one second portion of the infrared image is captured by the at least one second portion of the infrared sensor, wherein the infrared image is captured by the infrared sensor when the at least one black body element is disposed in front of the detector;

determine a plurality of calibration parameters for the infrared sensor based on the comparison, wherein each of the plurality of calibration parameters corresponds to one of the plurality of portions of the infrared sensor; and create a calibration table, wherein the calibration table includes the plurality of calibration parameters for the plurality of portions of the infrared sensor, wherein the calibration table and the plurality of calibration parameters adjust for bias of the infrared sensor when utilized for calibrating the radiometric camera.

2. The radiometric camera of claim 1, further comprising: the at least one black body element, wherein the at least one black body element is disposed in front of the detector.

3. The radiometric camera of claim 2, further comprising: a window, wherein the at least one black body element is disposed on the window, wherein the window further comprises a transparent member and at least one set of conductive pads, wherein the transparent member is made of a low conductivity material and is transparent at least with respect to the long wavelength infrared spectrum, and wherein each conductive pad is made of a high conductivity material such that the window is heated by resistive heating when a current is run through the at least one set of conductive pads.

4. The radiometric camera of claim 1, further comprising: a lens disposed in front of the detector with respect to the direction of the infrared sensor, the lens having an outer surface, wherein the outer surface of the lens is adapted to receive the at least one black body element such that the at least one black body element affects radiation readings by the at least one first portion via irradiating a pattern on the at least one first portion when the at least one black body element is disposed in the radiometric camera.

5. The radiometric camera of claim 1, wherein the processing circuitry is further configured to:

measure a temperature of the at least one black body element, wherein the plurality of calibration parameters is determined based further on the measured temperature of the at least one black body element.

6. The radiometric camera of claim 5, wherein the processing circuitry is further configured to:

heat the at least one black body element to a predetermined temperature such that the measured temperature of the at least one black body element is approximately the predetermined temperature, wherein the plurality of calibration parameters is determined based further on the predetermined temperature.

7. The radiometric camera of claim 6, wherein the radiometric camera further includes at least one heating element, wherein each heating element is disposed adjacent to one of the at least one black body element, wherein the at least one black body element is heated by raising a temperature of the at least one heating element.

8. The radiometric camera of claim 1, wherein the plurality of calibration parameters includes, for each pixel of infrared images captured by the radiometric camera, at least one of: gain, offset, and drift.

9. The radiometric camera of claim 1, wherein the infrared image is a first infrared image, wherein the processing circuitry is further configured to:

measure a temperature of each of at least one object shown in a second infrared image based on the sensor calibration table and the plurality of calibration parameters.

10. The radiometric camera of claim 9, wherein the processing circuitry is further configured to:

apply the calibration table to a plurality of temperature values of the second infrared image in order to determine a plurality of calibrated temperature measurements, wherein the temperature of the at least one object shown in the second infrared image is determined based on the plurality of calibrated temperature measurements.

11. The radiometric camera of claim 9, wherein the at least one object includes a plurality of objects, wherein the temperatures measured for the plurality of objects are measured simultaneously.

12. The radiometric camera of claim 9, wherein each of the at least one object is a human, wherein the measured temperature of each of the at least one object is a body temperature.

13. A method for calibrating a radiometric camera having internal black body components, comprising:

comparing at least one first portion of an infrared image captured by a radiometric camera with at least one second portion of the infrared image, the radiometric camera including an infrared sensor having a plurality of portions including at least one first portion and at least one second portion, wherein the infrared sensor is pointed in a direction, wherein the radiometric camera is adapted to receive at least one black body element in front of a detector containing the infrared sensor with respect to the direction of the infrared sensor, wherein the at least one black body element blocks radiation to the at least one first portion of the infrared sensor, wherein the at least one black body element does not block radiation to the at least one second portion of the infrared sensor, wherein the at least one first portion of the infrared image is captured by the at least one first portion of the infrared sensor, wherein the at least one second portion of the infrared image is captured by the at least one second portion of the infrared sensor, wherein the infrared image is captured by the infrared sensor when the at least one black body element is disposed in front of the detector;

determining a plurality of calibration parameters for the infrared sensor based on the comparison, wherein each of the plurality of calibration parameters corresponds to one of the plurality of portions of the infrared sensor; and creating a calibration table, wherein the calibration table includes the plurality of calibration parameters for the plurality of portions of the infrared sensor, wherein the calibration table and the plurality of calibration parameters adjust for bias of the infrared sensor when utilized for calibrating the radiometric camera.

14. The method of claim 13, further comprising:
measuring a temperature of the at least one black body element, wherein the plurality of calibration parameters is determined based further on the measured temperature of the at least one black body element.

15. The method of claim 14, further comprising:
heating the at least one black body element to a predetermined temperature such that the measured temperature of the at least one black body element is approximately the predetermined temperature, wherein the plurality of calibration parameters is determined based further on the predetermined temperature.

16. The method of claim 15, wherein the radiometric camera further includes at least one heating element, wherein each heating element is disposed adjacent to one of the at least one black body element, wherein the at least one black body element is heated by raising a temperature of the at least one heating element.

17. The method of claim 13, wherein the plurality of calibration parameters includes, for each pixel of infrared images captured by the radiometric camera, at least one of: gain, offset, and drift.

18. The method of claim 13, wherein the infrared image is a first infrared image, further comprising:
measuring a temperature of each of at least one object shown in a second infrared image based on the sensor calibration table and the plurality of calibration parameters.

19. The method of claim 18, further comprising:
applying the calibration table to a plurality of temperature values of the second infrared image in order to determine a plurality of calibrated temperature measurements, wherein the temperature of the at least one object shown in the second infrared image is determined based on the plurality of calibrated temperature measurements.

20. The method of claim 18, wherein the at least one object includes a plurality of objects, wherein the temperatures measured for the plurality of objects are measured simultaneously.

21. The method of claim 18, wherein each of the at least one object is a human, wherein the measured temperature of each of the at least one object is a body temperature.

22. A radiometric camera, comprising:
a detector, the detector further comprising a thermal detector configured to capture thermal images, wherein the thermal detector is pointed in a direction, wherein the radiometric camera is adapted to receive at least one black body element in front of the detector with respect to the direction of the thermal detector, the thermal detector having a plurality of portions including at least one first portion, wherein the at least one black body element affects radiation readings by the at least one first portion of a plurality of portions of the thermal detector when disposed in the radiometric camera;
wherein the plurality of portions of the thermal detector further include at least one second portion,
wherein the at least one black body element affects radiation readings by the at least one first portion via blocking the at least one first portion, and
wherein the at least one black body element does not block radiation to the at least one second portion.

23. The radiometric camera of claim 22, further comprising:
the at least one black body element, wherein the at least one black body element is disposed in front of the detector; and
a window, wherein the at least one black body element is disposed on the window, wherein the window further comprises a transparent member and at least one set of conductive pads, wherein the transparent member is made of a low conductivity material and is transparent at least with respect to the long wavelength infrared spectrum, wherein each conductive pad is made of a high conductivity material such that the window is heated by resistive heating when a current is run through the at least one set of conductive pads.

24. The radiometric camera of claim 22, further comprising:
a lens disposed in front of the detector with respect to the direction of the thermal detector, the lens having an outer surface, wherein the outer surface of the lens is adapted to receive the at least one black body element such that the at least one black body element affects radiation readings by the at least one first portion via irradiating a pattern on the at least one first portion when the at least one black body element is disposed in the radiometric camera.

* * * * *